(12) United States Patent
Nieuwenhuijsen

(10) Patent No.: US 8,337,820 B2
(45) Date of Patent: Dec. 25, 2012

(54) COMPOSITION OF A WATER-SOLUBLE SUNSCREEN PREPARATION FOR ACNE ROSACEA

(76) Inventor: Bart Nieuwenhuijsen, Penn Valley, PA (US)

( * ) Notice: Subject to any disclaimer, the term of this patent is extended or adjusted under 35 U.S.C. 154(b) by 0 days.

(21) Appl. No.: 13/506,801

(22) Filed: May 17, 2012

(65) Prior Publication Data

US 2012/0230929 A1 Sep. 13, 2012

Related U.S. Application Data

(63) Continuation-in-part of application No. 12/371,327, filed on Feb. 13, 2009, now Pat. No. 8,216,555.

(60) Provisional application No. 61/028,285, filed on Feb. 13, 2008.

(51) Int. Cl.
*A61K 8/18* (2006.01)
*A61Q 17/04* (2006.01)

(52) U.S. Cl. ............................................ 424/60; 424/59

(58) Field of Classification Search ........................ None
See application file for complete search history.

(56) References Cited

U.S. PATENT DOCUMENTS

| | | | | |
|---|---|---|---|---|
| 4,193,989 | A | * | 3/1980 | Teng et al. .................... 424/60 |
| 5,514,437 | A | * | 5/1996 | Tanner et al. .................. 424/63 |
| 5,603,923 | A | * | 2/1997 | Robinson et al. .............. 424/60 |
| 5,972,993 | A | * | 10/1999 | Ptchelintsev .................. 514/449 |
| 7,262,158 | B1 | * | 8/2007 | Lukenbach et al. .......... 510/122 |
| 2003/0031634 | A1 | * | 2/2003 | Grune ............................ 424/59 |
| 2004/0081681 | A1 | * | 4/2004 | Vromen ........................ 424/449 |
| 2004/0167046 | A1 | * | 8/2004 | Lukenbach et al. .......... 510/135 |
| 2005/0196361 | A1 | * | 9/2005 | Grune ............................ 424/59 |
| 2005/0209130 | A1 | * | 9/2005 | Patt ................................ 514/6 |
| 2006/0233725 | A1 | * | 10/2006 | Grune ............................ 424/59 |
| 2007/0243271 | A1 | * | 10/2007 | Hernandez et al. .......... 424/729 |
| 2009/0047310 | A1 | | 2/2009 | Meybeck |

OTHER PUBLICATIONS

Levy, Stanley B., MD; Tanning Preparations; Dermatologic—Medical Journal Clinics; Oct. 2000; 7 pages; vol. 18, Issue 4; W.B. Sanders Company; Unknown (presumed U.S.).

Petersen, Anita B. et al.; Dihydroxyacetone, the active browning ingredient in sunless tanning lotions, induces DNA damage, cell-cycle block and apoptosis in cultured HaCaT keratinocytes; Mutation Research (Genetic Toxicology and Enviromental Mutagenesis); 2004 (Received Jan. 30, 2003, received in revised form Feb. 14, 2004, accepted Mar. 4, 2004); pp. 173-186; 560 (2004); Elsevier B.V.; Unknown.

Jung, K.; UV-generated free radicals (FR) in skin; Their prevention by sunscreens and their induction by self-tanning agents; Spectrochimica Acta Part A; Copyright 2007 (Received Aug. 23, 2007; accepted Sep. 17, 2007); pp. 423-1428; Part A 69 (2008); Elsevier B.V.; Unknown.

Unknown author(s); Dihydroxyacetone; Wikipedia; Downloaded Jan. 2012 from http://www.wikipedia.org/; Unknown date of first publication.

Landers et al.; Contact urticaria, allergic contact dermatitis, and photoallergic contact dermatitis from oxybenzone; Am J Contact Dermat.; Mar. 2003; 14(1): 3304.

Nedorost, Susan T.; Facial erythema as a result of benzophenone allergy; J Am Acad Dermatol; vol. 49, No. 5; Nov. 2003; S259-S261.

* cited by examiner

*Primary Examiner* — Robert A Wax
*Assistant Examiner* — Olga V Tcherkasskaya
(74) *Attorney, Agent, or Firm* — Stephen G. Stanton, Esq.

(57) ABSTRACT

A topical skin care dihydroxyacetone-free final gel formulation to protect skin from ultraviolet rays comprising dispersed: titanium dioxide; 5-hydroxy-tryptophan; histidine; and N-acetyl-tyrosine.

11 Claims, No Drawings

COMPOSITION OF A WATER-SOLUBLE SUNSCREEN PREPARATION FOR ACNE ROSACEA

This Continuation-in-Part application claims benefit of application Ser. No. 12/371,327 filed Feb. 13, 2009 now U.S. Pat. No. 8,216,555 which in turn claimed benefit of Provisional Application Ser. No. 61/028,285 filed Feb. 13, 2008.

FIELD OF THE INVENTION

The present invention relates to skin care products, and specifically to sunscreen preparations.

BACKGROUND OF THE INVENTION

Sunscreen formulation are used to reduce the effects of harmful rays of the sun during sun tanning and/or exposure to the sun. Those with pre-existing skin conditions, such as acne rosacea, may have a greater susceptibility to exposure to the sun's rays.

SUMMARY OF THE INVENTION

This invention relates to a composition of a water-soluble sunscreen preparation for acne rosacea. The invention is a topical skin care dihydroxyacetone-free final gel formulation comprising dispersed titanium dioxide (titanium (IV) oxide), 5-hydroxy-tryptophan, histidine, and N-acetyL-tyrosine.

The present formulation is a topical skin care treatment that is water soluble and protects individuals with (acne) rosacea, or other sensitive skin types, from harmful UV rays without the use of chemical sunscreen ingredients that can cause an increase in skin inflammation, skin flushing and skin erythema (Nedorost (2003) and Landers et al., 2003).

DETAILED DESCRIPTION OF THE PREFERRED EMBODIMENT

This invention relates to a composition of a water-soluble sunscreen preparation for acne rosacea. The invention is comprised of the following components:

(1) Titanium dioxide (CAS number: 13463-67-7). The present formulation contains Titanium dioxide (Titanium (IV) oxide), chemical formula TiO2, dispersed in the final gel at a concentration of about 1% to about 8%. Titanium dioxide is a white solid mineral that is not soluble in water. Titanium dioxide has a very high refractive index (n=2.7) and is used in the present formulation to reflect harmful UV rays, (2) 5-Hydroxy-Tryptophan. The present formulation contains *Griffonia simplicifolia* extract, which naturally contains 5-Hydroxy-Tryptophan. The present formulation includes *Griffonia simplicifolia* extract at a concentration of about 0.2% to about 3% (w/v, using dried extract). 5-Hydroxy-Tryptophan is a natural amino acid that absorbs UV rays. The present formulation uses *Griffonia simplicifolia* extract since it naturally contains 5-Hydroxy-Tryptophan and because *Griffonia simplicifolia* extract adds a light brown color to the final preparation, which makes it easier to blend the sunscreen preparation with the color of the skin (since Titanium dioxide is pure white), (3) Histidine (CAS number 71-00-1). Histidine is used in the present formulation at a concentration of about 0.5% to about 3%. Histidine is a natural amino acid that absorbs UV rays, and (4) N-AcetyL-Tyrosine. N-AcetyL-Tyrosine is an acetylated derivative of the essential amino acid L-Tyrosine and is used in the present formulation in place of L-Tyrosine, due to its greater solubility in water. The formulation includes N-AcetyL-Tyrosine at a concentration of about 0.5% to about 5%.

The present formulation is a topical skin care treatment that is water soluble and protects individuals with (acne) rosacea, or other sensitive skin types, from harmful UV rays without the use of chemical sunscreen ingredients that can cause an increase in skin inflammation, skin flushing and skin erythema (Nedorost (2003) and Landers et al., 2003). Such chemical sunscreen ingredients are often used in waterproof sunscreens or sunblock preparations and include: p-aminobenzoic acid (PABA), oxybenzone, dioxybenzone, avobenzone, octyl methoxycinnamate, octocrylene, octyl salicylate, sulisobenzone.

One explicit example of a chemical that can negatively affect the skin of the user is dihydroxyacetone (DHA) and so would not be included in the inventive formulation. Further, DHA is also the ingredient in artificial tanning formulations/ agents that discolors the skin and so strives to give a user's skin a "natural" tan hue. Thus, the inventive formulation is dihydroxyacetone-free.

In the present formulation, Titanium dioxide (dispersed in the gel) will reflect UV rays and a blend of amino acids 5-Hydroxy-Tryptophan, Histidine and N-AcetyL-Tyrosine will absorb UV rays that have not been reflected.

*Griffonia simplicifolia* extract is available as a "5 HTP POWDER", (described as "5-HYDROXY, (5-HTP) from the herb *Griffonia simplicifolia*") when searching for "*Griffonia simplicifolia*" at the website of Beyond A Century, Inc. of 173 Lily Bay Road, Greenville, Me. 04441 (http://www.easycart-.net/BeyondACenturyInc./Aminos M-Z.html#0335). Also, 5-HTP is available (*Griffonia simplicifolia*) from a number of manufacturers, for example, at "iherb.com" (e.g., http://www.iherb.com/Healthy-Origins-Natural-5-HTP-100-mg-120-Capsules/14472?at=0). One skilled in the art would understand how to source the *Griffonia simplicifolia* extract that naturally contains 5-Hydroxy-Tryptophan.

The formulation is used by applying a thin layer of the sunscreen preparation to the entire face. When the application is still wet, the individual will be able to see the Titanium dioxide particles, which will enable the individual to determine if enough sunscreen is applied. Since the formulation is water-soluble (with Titanium dioxide particles dispersed throughout), it will need to be re-applied after sweating and swimming. Under dry conditions, the present formulation will provide protection from harmful UV rays for up to 2 hours, depending on the time of day and geographical location. The present formulation is a topical skin care treatment to protect the skin from harmful UV rays. The formulation is water-soluble and is gel-based, which consists of a polymer of Carbomer-940 neutralized with triethanolamine.

The formulation can be structured differently by dissolving titanium dioxide, 5-Hydroxy-Tryptophan, Histidine and N-AcetyL-Tyrosine in a different water-soluble gel base, which can be either Carbomer-based (including but not limited to: Carbomer 672, Carbomer 690, Carbomer 910, Carbomer 934, Carbomer 941, Carbomer 1342 or Carbomer 1622) or natural (including but not limited to: xanthan gum or guar gum). Additionally, the formulation can be structured differently by using Tryptophan instead of 5-Hydroxy-Tryptophan and L-Tyrosine instead of N-AcetyL-Tyrosine, although Tryptophan and L-Tyrosine are more hydrophobic than 5-Hydroxy-Tryptophan and N-AcetyL-Tyrosine. Furthermore, the present formulation can be structured differently by including the amino acid phenylalanine (although the present inventor does not include phenylalanine in the present formulation due to health risks). It can also be stated that a similar objective may be reached by including peptides containing the amino acids Tryptophan, Tyrosine, Histidine and Phenylalanine in various forms. The above-mentioned peptides can be made more water-soluble by adding polar side group to the amino acids.

The present invention may also be beneficial in protecting other sensitive skin types from UV rays. These sensitive skin types include, but are not limited to, skin disorders such as psoriasis, contact dermatitis, acne vulgaris (regular acne).

While particular embodiments of the present invention have been illustrated and described, it is not intended to limit the invention, except as defined by the following claims.

I claim:

1. A topical skin care dihydroxyacetone-free gel formulation to protect skin from ultraviolet rays comprising dispersed:
   titanium dioxide;
   5-hydroxy-tryptophan;
   histidine; and
   N-acetyl-tyrosine.

2. The formulation of claim 1 comprising
   about 1 to about 8% w/v of the titanium dioxide;
   about 0.2 to about 3.0% w/v of the 5-hydroxy-tryptophan;
   about 0.5% to about 3.0% w/v of the histidine; and
   about 0.5 to about 5.0% w/v of the N-acetyl-tyrosine.

3. The formulation of claim 2 wherein the 5-hydroxy-tryptophan is from the *Griffonia simplicifolia* extract.

4. The formulation of claim 1 wherein the formulation is non-comedogenic.

5. The formulation of claim 1 wherein the formulation is free of oils.

6. The formulation of claim 1 wherein the formulation is free of silicone.

7. The formulation of claim 1 wherein the formulation is free of parabens.

8. The formulation of claim 1 wherein a vehicle for the formulation includes water.

9. The formulation of claim 1 wherein the formulation contains a carbomer gelling agent.

10. The formulation of claim 1 wherein the formulation is water-soluble.

11. The formulation of claim 1 wherein the formulation will not increase rosacea symptoms.

* * * * *

UNITED STATES PATENT AND TRADEMARK OFFICE
CERTIFICATE OF CORRECTION

PATENT NO. : 8,337,820 B2
APPLICATION NO. : 13/506801
DATED : December 25, 2012
INVENTOR(S) : Bart Nieuwenhuijsen Page 1 of 1

It is certified that error appears in the above-identified patent and that said Letters Patent is hereby corrected as shown below:

In the Specification:

(1) Column 1, line 17, please replace "formulation" with -- formulations --.

(2) Column 2, line 30, please replace "5-HYDROXY, (5-HTP)" with
-- 5-HYDROXY-TRYPTOPHAN, (5-HTP) --.

In the Claims:

Column 4, line 7 (the second line of dependent claim 3), please replace "is from the Griffonia simplicifolia extract" with -- is from *Griffonia simplicifolia* extract -- (with "Griffonia simplicifolia" being in italics).

Signed and Sealed this
Twenty-sixth Day of February, 2013

Teresa Stanek Rea
*Acting Director of the United States Patent and Trademark Office*